United States Patent [19]

Smith et al.

[11] Patent Number: 4,604,384

[45] Date of Patent: Aug. 5, 1986

[54] PHARMACEUTICAL GEL COMPOSITION

[76] Inventors: Robert A. Smith, 42 Bigge Street, Liverpool, New South Wales, 2170; Maxine Goodman, 8/95 Chiswick Road, Greenacre, New South Wales 2190, both of Australia

[21] Appl. No.: 584,941

[22] PCT Filed: Jun. 21, 1983

[86] PCT No.: PCT/AU83/00081

§ 371 Date: Jan. 23, 1984

§ 102(e) Date: Jan. 23, 1984

[87] PCT Pub. No.: WO84/00111

PCT Pub. Date: Jan. 19, 1984

[30] Foreign Application Priority Data

Jun. 24, 1982 [AU] Australia ............................... PF4583

[51] Int. Cl.[4] ............................................ A61K 31/56

[52] U.S. Cl. .................................... 514/179; 514/171

[58] Field of Search ................ 424/240, 243; 514/179, 514/171

[56] References Cited

U.S. PATENT DOCUMENTS

| | | | |
|---|---|---|---|
| 4,131,677 | 12/1978 | Shen et al. | 424/256 |
| 4,360,518 | 11/1982 | Rovee et al. | 424/240 |
| 4,393,076 | 7/1983 | Noda et al. | 424/317 |

*Primary Examiner*—Elbert L. Roberts
*Attorney, Agent, or Firm*—Nies, Webner, Kurz & Bergert

[57] ABSTRACT

A composition for use for the treatment of burns, cuts, wounds, abrasions and the like, comprises a pharmaceutically acceptable glycol, preferably propylene glycol, and a cellulose derivative, which is heat sterilizable, preferably hydroxyethyl cellulose. The composition optionally contains an antiseptic, an antibiotic and/or a topical corticosteroid.

19 Claims, No Drawings

PHARMACEUTICAL GEL COMPOSITION

TECHNICAL FIELD OF THE INVENTION

The present invention relates to a pharmaceutical gel which may be used for the topical treatment of burns, cuts, wounds, abrasions and the like and to a method of treatment of burned skin.

BACKGROUND ART

The treatment of burns, and especially of major burns, leaves much to be desired. It is difficult to avoid the formation of keloid tissue with consequent contractures and detrimental effect on muscle movement recovery. Combating infection is also difficult, particularly when the site of infection is shielded for example by burn eschar.

In the treatment of burns it is usual to combat infection by use of compositions comprising one or more active ingredient in an inert pharmaceutical carrier.

The active ingredient is typically an antibiotic such as neomycin sulphate or micronized silver sulphadiazine; an anti-bacterial agent such as cetrimide chlorhexidine gluconate or dibromopropamide isethionate, and for minor burns a local anaesthetic such as lignocaine or a mixture of such ingredients.

The inert carrier or vehicle is commonly selected having regard to the solubility of the active constituent to be carried and for those mentioned above is usually a paraffin base ointment or an oil-in-water emulsion cream. For minor injuries, lanolin and petrolatum bases have been used. Aqueous gels, such as those formed with hydroxy methyl cellulose or polyacrylic acid have not hitherto found favour for treatment of injuries where there is skin lesion or for burns.

In pharmaceutical compositions of the type discussed each of the active ingredients performs its expected function. In addition to acting as a vehicle for the active ingredient, the inert carrier in many such preparations acts as a barrier to moisture transpiration.

As a general rule neither the active ingredient nor the vehicle plays any therapeutic part in skin regrowth. Possible exceptions are the use in such compositions of paraffin which has been said to promote the rapid formation of granulation tissue and the inclusion in some compositions of allantoin which has been said to aid tissue regeneration.

Many of the compositions hitherto used cause stains to dressings or linen (e.g. Furacin stains yellow, silver sulfadiazine stains black) and some cause pain on application (e.g. sulfamylon and to a lesser degree silver sulphadiazine) and/or have a degree of toxic reaction.

DISCLOSURE OF THE INVENTION

According to one aspect the present invention consists in a composition for use in the treatment of burns, cuts, wounds, abrasions and the like consisting of a heat sterilizeable aqueous gel comprising a pharmaceutically acceptable glycol and a cellulose derivative which is heat sterilizeable.

For preference the glycol is propylene glycol, and comprises from 20–30% W/V of the composition. Desirably the cellulose derivative is hydroxy ethyl cellulose and is used in an amount of less than 4% W/V of the composition. For preference also the composition comprises an antiseptic or an antibiotic or a topical corticosteroid or a combination of one or more of such agents.

According to a second aspect the invention consists in a method for treatment of a burn comprising the step of topical application of a composition according to the first aspect.

When an aqueous gel according to the invention is applied to a burned, cut, wounded or abraded skin surface an adherent flexible set jelly is formed, the depth and strength of which can be controlled by the number of coats applied.

Once formed the jelly acts as an effective barrier to contamination and mechanical interference.

Surprisingly, use of the composition as a treatment for burns has reduced the number of skin grafts that would otherwise have been necessary and has inhibited or prevented the formation of hypertrophic scar tissue so that most patients retain full (normal) muscle movement after healing. The coating allows for normal growth of facial hair in the male and on completion of re-epithelisation the coating lifts off spontaneously.

Preferred compositions according to the invention are colourless and may be applied liberally to a patient without staining of clothes.

The composition can be heat sterilized by autoclaving and is believed to exert an inherent bacteriostatic action and to have a degree of activity against a range of viruses or mycellia. It is effective as the sole agent in the treatment of clean superficial burns, cuts, wounds, abrasions and the like.

An advantage of compositions according to the invention is their ability to accept a wide range of agents which can be added for treatment of contaminated or infected wounds in accordance with sensitivity patterns revealed by bacterial culture for the individual patient.

For preference the composition includes one or more antibiotic or antiseptic or other agent. The jelly greatly augments penetration of non-vital tissue such as burn eschar and granulations by antibiotics and other agents and in the case of burns allows the effective destruction of pathogenic flora from burned areas by carrying the active agent to the depths of the burn. Release of the active agent is thought to be controlled by the physical nature of the gel.

PREFERRED EMBODIMENTS OF THE INVENTION

By way of example only various embodiments of the invention will now more particularly be described.

A preferred composition in accordance with the invention is:

| | Percentages W/W |
|---|---|
| AR grade Propylene glycol | 25.0% |
| Hydroxy ethyl cellulose | 2.0% |
| Sodium chloride | 0.9% |
| Distilled water | 72.1% |
| | 100.0% |

Ethylene glycol is usually considered to be pharmacologically unacceptable. Propylene glycol is preferred as the glycol component of the composition. However it is believed that other pharmaceutically acceptable glycols having more than three carbon atoms could be substituted for propylene glycol.

If the amount of propylene glycol present exceeds 30% W/V of the compound there is a tendancy for the composition to sting some patients. As the proportion of propylene glycol is reduced below 30% W/V the propensity to cause stinging is reduced. At 25.0% propylene glycol the incidence of reported stinging was acceptably low. At concentrations of propylene glycol below 15% W/V a deterioration in effectiveness is noticed and therefore concentrations greater than 15% and desirably greater than 20% are preferred. The range from 22.5–27.5% W/V is still more highly preferred.

The hydroxy ethyl cellulose is importantly a heat sterilizable substance which forms a gel with water and the amount required is chosen having regard to the desired consistency of the gel. From 0.5 to 4% W/V is a preferred range and more preferably from 1% to 3% W/V. Other gel-forming heat sterilizable celluloses may be used. However hydroxy ethyl cellulose available from A. C. Hatrick under the name Natrosol was found to more readily form a gel of suitable and smooth consistency with the propylene glycol and in contrast to hydroxy methyl cellulose and was found to retain a satisfactory gel structure after sterilization by autoclaving.

The inclusion of sodium chloride in the composition is optional and also serves to reduce stinging when the gel is applied on raw areas. The amount of salt present is preferably within the range of 0–2%.

By way of example of a method of preparation of the gel, the formulation hydroxy ethyl cellulose is first dispersed in the formulation propylene glycol. The salt, if any, is dissolved in the formulation water which is heated to approximately 60° C. The hydroxy ethyl cellulose/propylene glycol dispersion is then stirred slowly into the water. Stirring and heating is maintained until thickened. The composition is then bottled and heat sterilized.

The gel compositions according to the present invention may also contain one or more specific additives such as the following:

1. Antiseptic which may be present in an amount from 0.02 to 1.0% w/v of the composition. Suitable examples are chlorhexidine acetate or chlorhexidine gluconate.

2. Antibiotic which may be present in an amount from 0.1 to 0.4% w/v of the composition. A suitable example is gentamicin sulphate.

3. Topical corticosteroid which has a variety of functions but in particular is an anti-inflammatory agent, and may be present in an amount of up to 1% w/w of the composition and preferably of from 0.4 to 0.6% w/v.

Hydrocortisone added in concentrations of 0.5% has been clearly shown to make the jelly dramatically effective in the treatment of sunburn, 1st degree burns, acute uticaria, insect bites and the like. Symptomatic relief occurs within several minutes and inflammation is typically suppressed within 24 hours.

Compositions according to the invention may be used as the main dressing agent in both major and minor burns and in the management of wounds such as varicose ulcers and bedsores. It is envisaged that such compositions could also be used in dermalogical preparations with the addition of suitable specific additives and for household use in the treatment of minor burns, sunburn, cuts, wounds, abrasions and the like.

When applied with tulle gras under gladwrap in closed dressings, the jelly maintains its physical state for up to five days and thus prevents adherance of dressings to raw surfaces and allows dressings to be carried out without gross discomfort and pain, thus minimising the need for dressings under general anaesthetic.

When used in repeated applications to exposed surfaces the jelly dries to a flexible impervious coating, reacts with the surface exudate of the wound and thereafter forms a firm bond which can be soaked off readily if desired, or left insitu to peel off spontaneously when re-epithelisation has occurred. Whilst insitu the coating is a highly effective barrier against bacterial contamination and mechanical abrasion. Crusting and scab formation is prevented and normal hair growth is permitted. (This is particularly pertinent in burns in the beard area of the male face). The jelly is effective in burns of the face and perineam, and in the after care of facial dermabrasion; greatly increasing patient comfort and greatly reducing the chance of bacterial contamination.

Properly administered (see treatment plan below), the jelly has been found to minimise the formation of hypertrophic scar formation in resolved deep dermal burns and in small areas of full thickness burns healed by secondary intention. It also promotes the formation of dense well vascularised sterile granulating as graft bed, graft take has been improved dramatically and secondary scar hypertrophy and graft contractures across flexor surface has been shown to be greatly reduced.

When applied to fresh wounds exhibiting capillary ooze eg. Graft donor sites and area of fresh dermabrasion, the jelly has been found to produce effective haemostasis within a few minutes, after application under tulle gras and application of pressure, thus eradicating the presence of dried blood clot, a source of discomfort and possible medicine for bacterial propogation.

The following case histories further illustrate methods of treatment according to the invention. References to "jelly" in the case histories refer to a composition according to the invention.

CASE HISTORIES

Case I

A 57 year old male with advanced obstructive airway disease suffered extensive oil scalds on the right hand and forearm and the anterior and medial surfaces of the thigh and leg.

The burns were assessed as mid and deep dermal with margins of superficial burn and areas of probable full thickness. In total the burned area was estimated as 12% of the body surface area.

The patient was admitted to Hospital and the following regime was instituted:

(a) Oral penicillin. Oral Vitamin C 1000 mg/day. Oral Zinc sulfate 200 mg/BD.
(b) Blistered areas (excluding the palm of the hand) were peeled and all areas were soaked clean with cool 2% Magnesium sulfate solution.
(c) The hand was enclosed in a sterile polythene bag filled with jelly with 40 mgs/100 mls of gentamycin. Active movements were encouraged from the outset and the limb was elevated.
(d) All other areas were dressed with sofratulle, jelly with 40 mgs gentamycin/100mls, gladwrap+occlusive dressing.

The hand dressing was to be changed daily, and all other dressings second daily.

When the possibility of a future skin graft was explained to the patient, he refused absolutely to consider submitting himself to surgery, became intransigent and several days later signed himself out of hospital. Arrangements were made for him to be managed as an outpatient in the hospital casualty department. The regime detailed above was continued. Random bacteriological swabs were taken weekly.

Within four weeks the areas of partial thickness skin loss had healed leaving areas of full thickness loss comprising 1.5% of body surface on the medial surface of the thigh and the antero-medial surface of the leg of 2%. The regime was continued, all areas had healed completely with good quality, albeit hairless skin within seven weeks.

The following significant points were noted:

(1) Two months after healing was complete, the skin in the areas of apparent full thickness loss remained pliable and apparently normal. There was no evidence of hypertrophic scar formation. p0 (2) At no stage were any pathogenic organisms cultured from the involved areas.

(3) The dressings remained clean and odourless.

(4) The patient suffered no pain after the initial twenty four hours.

Case II

A male, aged 48, of Scottish extraction was trapped by the left leg in the wreckage of a burning car. Upon rescue and admission to Hospital it was noted that he had suffered very severe flame burns to the anterior medial and lateral surfaces of the leg from a point 30 cms below the knee joint and similar burns to the ankle and foot with partial sparing of the posterior two thirds of the plantar surfaces of the foot and the achilles section of the posterior heel, where deep dermal burns were present. Limited escharotomies were carried in the region of the ankle to preserve the vascular supply to the foot and a conservative regime similar to the one details in Case I was instituted and continued for one week. The patient was then taken to theatre for debridement and exploration. On exploration the following was noted:

(1) The distal phalanx of the great toe was completely destroyed.

(2) The extensor tendons to the toes were destroyed throughout the length of their course on the dorsal surface of the foot.

(3) The peroneal tendons and the tendon of the tibealis anterior were severely damaged.

(4) The muscles in the anterolateral and anteromedial sections of the lower calf were severely damaged.

(5) The extensor retinaculan was destroyed and the associated tendons exposed and severely damaged.

(6) The subcutaneous section of the tibia was charred and apparently avascular in its lower two thirds. There was similar exposure of the dorsal surfaces of several of the tarsal bones and the dorsal surfaces of several metatarsals.

(7) Sensation to the sole of the foot was subsequently shown to have been largely spared.

Non vital tissue was cleared to reveal extensive areas of bare burnt bone and large areas of badly burned apparently avascular tendon.

Thereafter dressings were carried out second daily. The patient was returned to theatre several times for decortication and drilling of the exposed bone. Bacteriological swabs were taken at weekly intervals.

After ten weeks a satisfactory graft base had been established and grafting was carried out. One hundred percent graft take was achieved and six months later the graft has settled and there is no evidence of hypertrophic scarring. The wounded area remained free of significant bacteriological contamination throughout the prolonged conservative management. Four other molten metal burns to the feet of a similar but slightly less severe nature are recorded in the series. All had a similar satisfactory outcome.

Case III

A twenty four year old male who was soaked with petrol and ignited by his wife as he lay drunk and asleep in bed.

He was admitted to Hospital B via Hospital A 12 hours after the incident with full thickness burns to the neck, trunk, shoulders, axillae, arms and anterior thighs. There were partial thickness burns on the lower back, buttocks, forearms and hands with sparing of the posterior thighs, lower legs and feet.

The patient had been coated with Silver Sulfadiazine at Hospital A and on admission a mixed flora of organisms including staphylococcus aureus and psuedomonas was cultured from multiple swabs.

The patient was barrier nursed and the regime of soaking with sterile magnesium sulfate solution and dressings with sofratulle, jelly with 40 mgs gentamycin/100mls, gladwrap, occlusive dressings was instituted. The hands were dressed in sterile plastic bags and the neck and perineam were kept open and dressed with jelly/gentamycin 80 mgs/100 mls. The problem presented in this case was the need to graft approximately 60% of the body surface area with a maximum of 30% available donor area with the areas of partial skin loss to be restored before the 30% donor area could be realised.

When the patient's condition permitted it the schar was cleared from the neck and axillae and five days later when viable sterile graft beds had been established, sheet grafts were tailored to shape and applied and tied over the proflavine wool saturated in jelly/40 mgs gentamycin. Dressings continued as before on all other areas, the patient being nursed on a Streicher frame.

Eight days later the dressings were taken down and 100% take of well established graft was recorded in the grafted areas.

All other areas were desloughed conservatively and grafted with thin postage stamps of skin as areas become ready to graft and donor skin became available. Grafted areas were closed with large tie-over dressings with profuse jelly/gentamycin 80 under the dressings to condition the granulated areas between the postage stamp grafts. The donor areas were dressed in the same way and in some areas were harvested twice.

The tie over dressings allowed access to the other areas for a continuation of the dressing regime at intervals of 48 hours.

The grafted areas were taken down usually after 7 or 8 days. In all instances the graft take was satisfactory and the inter graft granulations remained healthy and free of pathogens. In many instances healthy epithelial outgrowth from the graft patches was noted at the time of the first dressing.

After 10 weeks the patient was almost completely healed and freely ambulant. Unfortunately, at this stage he began receiving visitors who supplied him with liquor. In the eleventh week he absconded without notice.

He returned for a medical certificate after a period of two and half years, much of the time having been spent in detention. In this time he had had no follow-up treatment.

On examination all grafted areas had resolved to pliable satisfactory skin. There was no evidence of hypertrophic scarring anywhere and no evidence of graft contracture. Movements of the shoulders were full and free and the contour of the throat was normal.

The significant points in Case III are as follows:

(a) When the patient was admitted 12 hours after the burn, having been treated with silver sulfadizine, cultures of psuedomonas and staphylococcus aureus were obtained.

These were rapidly controlled and although staphylococcus albus, staphylococcus epidermatitis, psuedomonas and diptherroids were from time to time cultured from the patient, at no time was there evidence of invasive infection; and in all areas, after the non-vital tissue had been eliminated, the granulations remained healthy and effectively sterile.

(b) At no stage did the patient suffer severe toxic fevers which have been considered almost inevitable in the course of burns of this magnitude.

(c) The dressings and burned areas remained clean and odourless throughout the course of management.

(d) The patient remained in satisfactory metabolic balance and did not exhibit the phenomenon of wasting which is probably due to the toxaemia associated with infected burns. Wasting has been considered inevitable in burns of this magnitude and is a commonly accepted cause of death.

(e) Despite the complete lack of follow-up care the patient achieved what can be quite fairly assessed as a spectacularly successful final recovery. The lack of the necessity for follow-up surgery is believed to represent a significant shift in the accepted norm of major burn management.

Case IV

A 72 year old female with periphical vascular disease presented with post thrombotic ulcers in the pretibial zone of the left leg.

On admission the ulcers were surrounded by intense cellulitis.

Bacteriological swabs showed a mixed flora of organisms including psuedomonas and a multiresistant staph, aureus.

A regime was commenced with magnesium sulph soakes and application of jelly with 1% chlorhexidine daily. Within five days the swabs were negative and chlorhexidine was replaced with dressings of plain jelly over sofra-tulle. Two surgical debridements were necessary and some weeks passed before a satisfactory graft bed was established but the areas did not exhibit any further bacterial growth.

Eventually grafting was carried out and 100% take was recorded. The patient was discharged to the care of a vascular surgeon completely healed.

Case V

A 22 year old male suffered extensive deep dermal burns to the lateral surfaces of the left thigh and calf from burning petrol in a motor bike accident.

For the first 10 days he was under the care of another surgeon and treated by the open method between sterile sheets with regular application of silver sulfadiazine. Consultation was sought when the leg became acutely inflamed and painful and the patient was running a high fever.

Bacteriological culture revealed a mixed growth of organisms including profuse staph, aureus. Sensivity tests showed this organism to be sensitive to gentamycin and the established routine detailed above was instituted using jelly/80 mgs gentamycin/100 mls, tulle and occlusive dressings twice daily until culture showed no growth and the inflammation, pain and fever had subsided after five days. The concentration of gentamycin was reduced to 40 mgs/100 mls and dressings were carried out daily and then second daily. There was no further bacterial invasion and healing without hypertrophic scarring was achieved in due course.

Case VI

A consultant anaesthetist developed an acute allergic uticaria on the torso and arms. He volunteered to have jelly with 0.5% hydrocortisone on the right side and betnovate cream of the left side. Within one hour there was significant symptomatic relief on the right side and within four hours the right side was clear. The rash was still present on the left side 12 hours later.

When one of the anaesthetists children was severely sunburned shortly afterwards, he applied the above preparation in a similar pattern. Again the jelly was dramatically more effective.

Modifications to and variations of both the composition and methods of treatment hereof such as would be apparent to those skilled in the art are deemed to be within the scope of the disclosure.

The claims defining the invention are as follows.

We claim:

1. A composition for use in the treatment of burns, cuts, wounds, abrasions and the like consisting essentially of, per 100 parts by weight of composition, from 20 to 30 parts by weight of propylene glycol, from 1 to 4 parts by weight of hydroxy ethyl cellulose, from 0 to 2 parts by weight of sodium chloride, and the balance water, said composition being substantially sterile.

2. A composition according to claim 1, further including an antibiotic.

3. A composition according to claim 2, further including an antiseptic.

4. A composition according to claim 3, further including a topical corticosteroid.

5. A composition according to claim 4, wherein the antiseptic is selected from the group consisting of chlorhexidine acetate and chlorhexidine gluconate.

6. A composition according to claim 5, wherein the antibiotic is gentamican sulphate.

7. A composition according to claim 6, comprising from 0.5% to 1.0% W/V of a topical corticosteroid.

8. A composition for use in the treatment of burns, cuts, wounds, abrasions and the like consisting essentially of, per 100 parts by weight of composition,:

from 20 to 30 parts by weight of propylene glycol, from 1 to 4 parts by weight of hydroxy ethyl cellulose, from 0 to 2 parts by weight of sodium chloride, from 0.1 to 0.4% of an antibiotic, and the balance of water, said composition being substantially sterile.

9. A composition according to claim 8, including a topical corticosteroid.

10. A composition according to claim 9, wherein the antibiotic is gentamican sulphate.

11. A composition according to claim 10, comprising from 0.5% to 1.0% W/V of the topical corticosteroid.

12. A composition for use in the treatment of burns, cuts, wounds, abrasions and the like consisting essentially of, per 100 parts by weight of composition,:

from 20 to 30 parts by weight of propylene glycol,
from 1 to 4 parts by weight of hydroxy ethyl cellulose,
from 0 to 2 parts by weight of sodium chloride,
from 0.5% to 1% W/V of a topical cortico steroid, and
the balance of water, said composition being substantially sterile.

13. A composition according to claim 12, further including an antiseptic.

14. A composition according to claim 13, wherein the antiseptic is selected from the group consisting of chlorhexidine acetate and chlorhexidine gluconate.

15. A method for the topical treatment of burns, cuts, abrasions, sores and the like which comprises the steps of topical application thereto of an aqueous pharmaceutical gel composition according to claim 1.

16. A method for the topical treatment of burns, cuts, abrasions, sores and the like which comprises the steps of topical application thereto of an aqueous pharmaceutic gel composition according to claim 2.

17. A method for the topical treatment of burns, cuts, abrasions, sores and the like which comprises the steps of topical application thereto of an aqueous pharmaceutical gel composition according to claim 8.

18. A method for the topical treatment of burns, cuts, abrasions, sores and the like which comprises the steps of topical application thereto of an aqueous pharmaceutical gel composition according to claim 12.

19. A method for the topical treatment of burns, cuts, abrasions, sores and the like which comprises the steps of topical application thereto of an aqueous pharmaceutic gel composition according to claim 7.

* * * * *